US010420715B2

(12) United States Patent
Zelkha et al.

(10) Patent No.: US 10,420,715 B2
(45) Date of Patent: Sep. 24, 2019

(54) CAROTENOID COMPOSITION AND METHOD FOR PROTECTING SKIN

(75) Inventors: Morris Zelkha, Omer (IL); Zohar Nir, Meitar (IL); Tanya Sedlov, Beer Sheva (IL)

(73) Assignee: Lycored Ltd., Beer-Sheva (IL)

(*) Notice: Subject to any disclaimer, the term of this patent is extended or adjusted under 35 U.S.C. 154(b) by 211 days.

(21) Appl. No.: 12/406,762

(22) Filed: Mar. 18, 2009

(65) Prior Publication Data

US 2009/0176872 A1 Jul. 9, 2009

Related U.S. Application Data

(63) Continuation of application No. 10/495,514, filed as application No. PCT/IL02/00875 on Nov. 5, 2002, now abandoned.

(30) Foreign Application Priority Data

Nov. 14, 2001 (IL) .......................................... 146496

(51) Int. Cl.
| | |
|---|---|
| *A61K 8/11* | (2006.01) |
| *A61K 8/02* | (2006.01) |
| *A61K 8/31* | (2006.01) |
| *A61K 8/67* | (2006.01) |
| *A61Q 17/00* | (2006.01) |
| *A23L 33/105* | (2016.01) |

(52) U.S. Cl.
CPC .............. *A61K 8/11* (2013.01); *A23L 33/105* (2016.08); *A61K 8/02* (2013.01); *A61K 8/0216* (2013.01); *A61K 8/31* (2013.01); *A61K 8/678* (2013.01); *A61Q 17/00* (2013.01); *A23V 2002/00* (2013.01)

(58) Field of Classification Search
CPC .......... A23V 2002/00; A23V 2250/213; A23V 2250/712; A61K 8/678
See application file for complete search history.

(56) References Cited

U.S. PATENT DOCUMENTS

| | | | |
|---|---|---|---|
| 3,920,834 A | 11/1975 | Klaui et al. | |
| 5,290,605 A | 3/1994 | Shapira | |
| 6,110,748 A | 8/2000 | Reber et al. | |
| 6,132,790 A * | 10/2000 | Schlipalius | 426/540 |
| 9,468,609 B2 | 10/2016 | Levy et al. | |
| 2002/0012714 A1* | 1/2002 | Olson | 424/766 |
| 2009/0326056 A1 | 12/2009 | Goralczyk et al. | |

FOREIGN PATENT DOCUMENTS

| | | | |
|---|---|---|---|
| CN | 2002/0012714 | | 1/2002 |
| JP | 2000060417 A | | 2/2000 |
| JP | 2010208972 A | | 9/2010 |
| WO | WO 97/48287 | * | 6/1997 ............. A23L 1/212 |
| WO | WO 00/13654 A2 | * | 3/2000 |
| WO | 0185182 A2 | | 11/2001 |
| WO | WO 02/058683 A2 | | 8/2002 |
| WO | 03068202 A1 | | 8/2003 |
| WO | 2004052351 A1 | | 6/2004 |
| WO | 2009007975 A1 | | 1/2009 |
| WO | 2007037438 A1 | | 4/2009 |
| WO | 2010082205 A1 | | 7/2010 |
| WO | 2011057183 A1 | | 5/2011 |

OTHER PUBLICATIONS

Paetau et al. (Am. J. Clin. Nutr. 1998, 68: 1187-1195).*
Kucuk et al., "Phase II Randomized Clinical Trial of Lycopene Supplementation Before Radical Prostatectomy", *Cancer Epidemiology, Biomarkers & Prevention*, vol. 10, pp. 861-868, Aug. 2001.
Paetau et al., "Chronic Ingestion of Lycopene-Rich Tomato Juice or Lycopene Supplements Significantly Increases Plasma Concentrations of Lycopene and Related Tomato Carotenoids in Humans" *American Journal of Clinical Nutrition*, vol. 68, pp. 1187-1195, 1998.
Stahl et al, "Dietary Tomato Paste Protects Against Ultraviolet Light-Induced Erythema in Humans", *Journal of Nutrition*, vol. 131, pp. 1449-1451, 2001.
About Lyc-O-Mato TM, Lyc-O-MATO® *Tomato Extract . . . It's Not Just Lycopene*, Online!, Retrieved From the Internet: on May 3, 2003 <URL: http://www.lycomato.com/>.
Healthy Origins-Lyc-O-Mato Clinical Trio Lycopene, 60 SoftGels, Online!, Retrieved From the Internet: on May 3, 2003 <URL: http://www.lifesvigor.com/products/378105.html>.
Paetau et al., "Chronic Ingestion of Lycopene-rich Tomato Juice or Lycopene Supplements Significantly Increases Plasma Concentrations of Lycopene and Related Tomato Carotenoids in Humans", Am. J. Clin. Nutr. (1968), vol. 68, pp. 1187-1195, XP-002233573.
Susanne Rath, et al. "Lycopene Extract From Tomato Chemical and Technical Assessment (CTA)" (at http://www.fao.org/fileadmin/templates/agns/pdf/jecfa/cta/71/lycopene_extract_from_tomato.pdf), 9 pages, (2006 or later).
O'Kennedy et al. "Effects of antiplatelet components of tomato extract on platelet function in vitro and ex vivo: a time-course cannulation study in healthy humans", Am J Clin Nutr 2006;84:570-9. Printed in USA. © 2006 American Society for Nutrition (10 pages).
USDA National Nutrient Database for Standard Reference Release 26, "Basic Report 11546, Tomato products, canned, paste, without salt added", Report Date:Oct. 22, 2013 15:09 EDT (2 pages).

(Continued)

*Primary Examiner* — Mina Haghighatian
*Assistant Examiner* — Mei Ping Chui
(74) *Attorney, Agent, or Firm* — Roach Brown McCarthy & Gruber, P.C.; Kevin D. McCarthy

(57) ABSTRACT

A method for protecting skin against damages caused by ultra-violet (uv) radiation from the sun, comprising administering to a subject in need of protection an effective amount of a composition containing lycopene from a natural source and one or more carotenoid selected from among phytoene and phytofluene or mixtures thereof.

5 Claims, 1 Drawing Sheet

(56) References Cited

OTHER PUBLICATIONS

Asim K. Dutta-Roy, Lynn Crosbie, Margaret J. Gordon (2001) Effects of tomato extract on human platelet aggregation in vitro, Platelets, 12:4, 218-227, Doi: 10.1080/09537100120058757 (11 pages).
Davies et al., "The constituents of tomato fruit—the influence of environment, nutrition, and genotype"; C R C Critical Reviews in Food Science and Nutrition, 205-280 Nov. 1981 (76 pages).
Gary R. Beecher, "Nutrient Content of Tomatoes and Tomato Products"; Exp Biol Med (Maywood) 1998 218: 98 (4 pages).
LycoRed Natural Products Industries Limited, LycoRed website, FAQ page, Jul. 21, 2001, URL: http:///www.lycored.com/FAQ1.jtml, Internet Archive Wayback Machine [online], URL,http://web.archive.org/web/20010619093210 / http://www.lycored.com/frame.cfm?page=3.
Japanese Office Action for Application No. 2012-104722, dated Sep. 3, 2013 (Translated into English).
Anonymous, "Higher Nature Astaxanthine and Balckcurrant Capsules Pack of 90: Amazon.co.uk: Health & Personal Care", Retrieved from the Internet—URL: http://www.amazon.co.uk/dp/B000NRVW2U?_encoding=UTF8&isInlframe=0&n=65801031&ref_=dp_rpddesc_0&s=drugsore&showDetailProductDesc=1#product-description_feature_div Published Feb. 26, 2007, pp. 1-6, as retrieved on Sep. 22, 2016 (6 pages).
Greenspan, D., "Salmon with Tomatoes & Rosemary", Retrieved from the Internet—URL: http://communitytable.parade.com/30359/doriegreenspan/salmon-with-tomatoes-rosemary/ Published 263 Jul. 2011, pp. 1-3, as retrieved on Sep. 22, 2016 (3 pages).
Ramses B. Toma et al; "Lycopene content in raw tomato varieties and tomato products"; Journal of foodservice; Apr. 1, 2008; vol. 19, pp. 127-132. (6 pages).
Ademoyegun Olufemi Temitope et al; "Lycopene Content in Tomatoes (Lycopersicon esculentum Mill): Effect of Thermal Heat and its Health Benefits"; Fresh Produce 2009 Global Science Books; Jan. 1, 2009; vol. 3(1), pp. 40-43. (4 pages).
Pratik M. Choksi et al; "A Review on Lycopene—Extraction, Purification, Stability and Applications"; International Journal of Food Properties; vol. 10, pp. 289-298, 2007. (10 pages).
Lee et al., "Astaxanthin inhibits nitric oxide production and inflammatory gene expression by suppressing IkB Kinase-dependent NF-KB Activation"; Molecules and Cells (Impact Factor: 2.09) Sep. 2003; 16(1):97-105. (9 pages).
Palozza et al., "Tomato Lycopene and Inflammatory Cascade: Basic Interactions and Clinical Implications"; Current Medicinal Chemistry, The New International Journal for Timely In-Depth Reviews in Medicinal Chemistry; vol. 17, No. 23; Aug. 2010; pp. 2547-2563. (2 pages).
Hadad et al., "The synergistic anti-inflammatory effects of lycopene, lutein, b-carotene, and carnosic acid combinations via redox-based inhibition of NF-kB signaling"; Free Radical Biology and Medicine; vol. 53, Issue 7, Oct. 1, 2012, pp. 1381-1391. (11 pages).
Rafi et al., "Dietary lutein modulates inducible nitric oxide synthase (iNOS) gene and protein expression in mouse macrophage cells (RAW 264.7)"; Molecular Nutrition & Food Research; vol. 51, Issue 3, pp. 333-340, Mar. 2007. (8 pages).
Rafi et al., "Lycopene Inhibits LPS-Induced Proinflammatory Mediator Inducible Nitric Oxide Synthase in Mouse Macrophage Cells"; Journal of Food Science; vol. 72; pp. 69-74, 2007. (6 pages).
Choi et al., "Inhibition of nNOS and COX-2 expression by lutein in acute retinal ischemia"; Nutrition; vol. 22, pp. 668-671, 2006. (4 pages).
Feng-Yao Tang et al: "Concomitant consumption of lycopene and fish oil inhibits tumor growth and progression in a mouse xenograft model of colon cancer"; Molecular Nutrition & Food Research; vol. 56, No. 10; Sep. 7, 2012; pp. 1520-1531. (12 pages).
Verschuren L et al: "A Dietary Mixture Containing Fish Oil, Resveratrol, Lycopene, Catechins, and Vitamins E and C Reduces Atherosclerosis in Transgenic Mice"; The Journal of Nutrition; vol. 141, No. 5; Mar. 16, 2011; pp. 863-869. (7 pages).
Garcia-Alonso F J et al: "Effect of consumption of tomato juice enriched with n-3 polyunsaturated fatty acids on the lipid profile, antioxidant biomarker status, and cardiovascular disease risk in healthy women"; European Journal of Nutrition; vol. 51, No. 4; Jul. 14, 2011; pp. 415-424. (10 pages).
Yasuno Fumihiko et al: "Combination of Antioxidant Supplements Improved Cognitive Function in the Elderly"; Journal of Alzheimer's Disease; vol. 32, No. 4; Aug. 2012; pp. 895-903. (9 pages).
https://recipe.rakuten.co.jp (11 pages) printed Dec. 13, 2017; actual publication date is unknown but according to the Wayback Machine at https://web.archive.org/web/2014*/recipe.rakuten.co.jp/recipe/1860005068, that was "Saved 1 time Nov. 15, 2014".
Ohata T. et al; "Suppression of Nitric Oxide Production in Lipopolysaccharide-stimulated Macrophage Cells by omega 3 Polyunsaturated Fatty Acids"; Jpn. J. Cancer Res; vol. 88, pp. 234-237, Mar. 1997. (5 pages).
Engelmann N. J et al; "Nutritional Aspects of Phytoene and Phytofluene, Carotenoid Precursors to Lycopene"; Am society for Nutrition; vol. 2, pp. 51-61, 2011 (11 pages).

\* cited by examiner

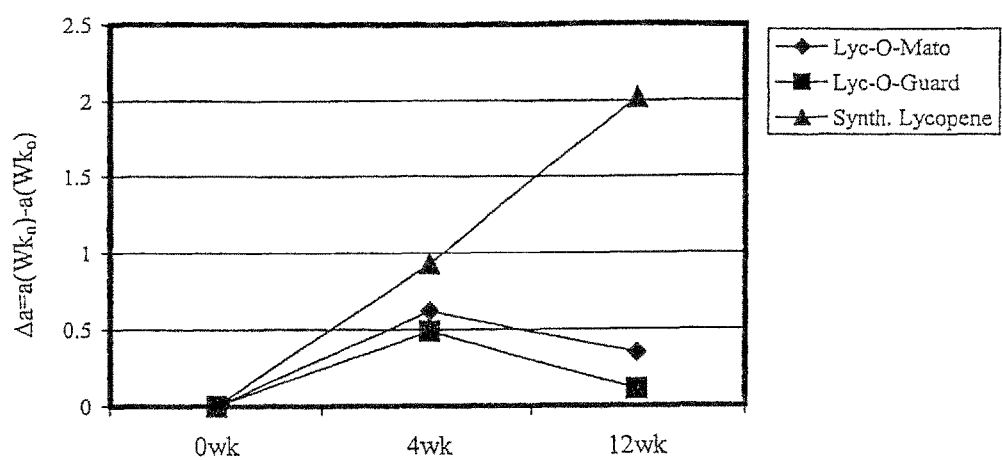

CAROTENOID COMPOSITION AND METHOD FOR PROTECTING SKIN

FIELD OF THE INVENTION

The present invention relates to the field of protection from sun radiation, particularly to methods and compositions effective in protecting skin.

BACKGROUND OF THE INVENTION

It is well established that prolonged exposure to sun has damaging effects on the skin. Particularly, the uv radiation from the sun is known to cause erythema of the skin, sunburn and skin cancer. Protection of the skin from uv radiation can be achieved by protective attire as well as by protection in the form of topical compositions of various protective ingredients. A particular group of protective compositions are intended for oral administration. Oral compositions contain active ingredients which are delivered to the skin via an internal transport mechanism and thus protect the skin from uv radiation damage. A particular group of active ingredients which are suitable for use with said oral compositions are carotenoids. U.S. Pat. No. 3,920,834 describes the use of a mixture of carotenoids wherein cathaxanthin is the primary carotenoid in the composition. However, the use of cathaxanthin is known to be limited due to adverse effects it may have on pigmentation. U.S. Pat. No. 5,290,605 describes food-stuff and beverages intended for providing protection to the skin against uv sun radiation. Said foodstuff and beverages comprising carotenoids as well as ascorbic acid, tocopherols, coenzyme Q10 and reduced glutathione. U.S. Pat. No. 6,110,478 further describes a composition for protecting skin against uv radiation and the harmful effects thereof, wherein the composition contains a pro-vitamin A carotenoid and lycopene. The use of such a composition is limited by the negative effect pro-vitamin A carotenoids may have on the subject's health at certain dosage levels. An excess of vitamin A, which is produced in the body from pro-vitamin A carotenoids, was found to have adverse effects on health. Stahl et al ("Dietary Tomato Paste Protects against Ultraviolet Light-induced Erythema in Humans", *Biochemical and Molecular Action of Nutrients, Research Communication*, (2001) 1449-1451) have shown the protective effect of tomato paste which is known to contain inter alia lycopene, β-carotene and tocopherol, against uv light-induced erythema. However, Stahl has reported a problem in achieving desired carotenoid serum levels, suggesting poor bioavailability.

Accordingly, there is a long felt need to develop a composition for protecting skin against uv radiation which is suitable for oral administration and is safe at a wide range of dosages.

It is therefore a purpose of the present invention to provide a method for protecting skin against damages caused by ultra-violet (uv) radiation from the sun.

A further purpose of the present invention is to provide a carotenoid composition effective in protecting the skin against the damages of uv radiation and which does present potential health risks.

It is yet another purpose of the present invention to provide a method and composition that overcome the disadvantages of the known art.

Other objectives of the invention will become apparent as the description proceeds.

SUMMARY OF THE INVENTION

The present invention provides a method for protecting skin against damages caused by ultra-violet (uv) radiation from the sun, comprising administering to a subject in need of protection an effective amount of a composition containing lycopene from a natural source and one or more carotenoid selected from among a group consisting of phytoene and phytofluene. Optionally, said composition may further contain vitamin E.

Further provided by the present invention is a composition comprising of 6% to 25% lycopene of a natural source and more than 0.3% of one or more carotenoid selected from among a group consisting of phytoene and phytofluene. Optionally, said composition may contain 1% to 4% vitamin E.

Further provided by the present invention is the use of a carotenoid composition containing lycopene from a natural source and one or more carotenoid selected from among a group consisting of phytoene and phytofluene as a protective agent against uv light-induced damage to skin. Optionally, said composition may further contain vitamin E.

The present invention further provides administration forms for the presently claimed composition, wherein said administration form may be a food-stuff, beverage or pharmaceutically acceptable dosage form.

DESCRIPTION OF THE DRAWINGS

FIG. 1 illustrates a comparison of protection of various carotenoid compositions against erythema (see Example 2 for clarifications of terms appearing in graph).

DETAILED DESCRIPTION OF A PREFERRED EMBODIMENT OF THE INVENTION

The following description is illustrative of embodiments of the invention. The following description is not to be construed as limiting, it being understood that the skilled person may carry out many obvious variations to the invention.

Throughout the description, percentages of components are by weight, unless specifically noted differently. The terms "lycopene of natural sources" and "natural lycopene" are synonymous throughout the application and refer to lycopene from vegetables, fruits, plant matter, fungus and fungal sources, and natural bio-mass.

It has surprisingly been found that carotenoid compositions which contain natural lycopene and one or more carotenoid selected from among a group consisting of phytoene and phytofluene, are effective in protecting skin against damages caused by uv radiation from the sun, wherein said damages are erythema and sunburn. Furthermore, unexpectedly, it has been found in the present invention that natural lycopene is significantly more effective in protecting skin against uv radiation damages than synthetic lycopene. A further surprising finding according to the present invention, is that the addition of phytoene and/or phytofluene to the natural lycopene composition improves the effectiveness of the composition in protecting skin against uv radiation damage.

According to an embodiment of the method of the present invention, 1 mg to 10 mg of a composition comprising 6% to 15% of natural lycopene and 0.3% to 1.5% of one or more carotenoid selected from among phytoene and phytofluene are administered to a subject. Preferably, about 5 mg of a composition comprising 6% of natural lycopene, 0.5% phytoene and 0.5% phytofluene are administered.

In yet a further embodiment of the present method the aforementioned compositions may contain 1.5% to 2.5% of vitamin E. preferably, said composition containing about 6% natural lycopene, 0.5% phytoene, 0.5% phytofluene and 2% vitamin E.

According to a particular embodiment of the invention, the compositions employed comprise natural lycopene and one or more additional carotenoid selected from among phytoene and phytofluene wherein the ratio between the lycopene and additional carotenoids is in the range of 20:1 to 5:1, preferably 8:1 to 5:1.

The indicated dosages refer to a healthy adult in the weight range of 50 Kg to 70 Kg and thus may vary according to body size. However, preferably, the dosage is adjusted so that the carotenoid serum level of the subject reaches a level within the range of 0.3 to 1.2 µM (micromole/liter), wherein serum levels of lycopene are 0.2 to 0.6 µM, phytoene 0.08 to 0.2 µM and phytofluene 0.08 to 0.4 µM. Dosages of total carotenoids may be daily in single or multiple doses, of about 2 to 15 mg/day, preferably 5 mg/day.

The compositions are administered by means known in the art, which will achieve the desired carotenoid serum levels. Oral administration is preferred. The oral administration can be in the form of a capsule, gel-cap, pellet, soft gel capsule or tablet which contain the carotenoid compositions. Said oral dosage forms may contain pharmaceutically acceptable excipients, additives, carriers and stabilizers. Particularly important additives are of the type which improve bioavailability of the carotenoids, e.g. oils and surfactants. Said oral dosage forms are prepared according to conventional methods known from the art. A preferred means of oral administration is via foodstuff and beverages. Thus, the carotenoid composition is added to foodstuff or beverages. The amount of carotenoid composition in the foodstuff and beverage is adjusted to meet the above-mentioned dosages.

According to a particular embodiment of the present method, administration of the composition is preferably started before exposure to uv radiation. Preferably, 7 to 30 days before exposure, and administration is continued during exposure.

According to a further aspect of the present invention there is provided a novel carotenoid composition comprising of 6% to 15% lycopene of a natural source and 0.3% to 1.5% of one or more carotenoid selected from among a group consisting of phytoene and phytofluene. Preferably, the composition comprises 6% of natural lycopene, 0.5% phytoene and 0.5% phytofluene.

According to yet a further embodiment the composition may further comprise of 1.5% to 2.5% vitamin E. Preferably the composition contains 6% natural lycopene, 0.5% phytoene, 0.5% phytofluene and 2% vitamin E.

The compositions of the present invention comprise natural lycopene and one or more additional carotenoid selected from among a group consisting of phytoene and phytofluene wherein the ratio between the lycopene and additional carotenoid is in the range of 20:1 to 5:1, preferably 8:1 to 5:1. Optionally, the composition may further contain vitamin E wherein the ratio between the lycopene and the vitamin E is in the range of 10:1 to 2:1, preferably 8:1 to 3:1.

A particular embodiment of the present invention relates to solid and liquid oral dosage forms selected from among a group comprising of a capsule, gel-cap, pellet, soft gel capsule, tablet, or other liquid or solid oral dosage forms known in the art, which comprises a carotenoid composition which contains 5 mg to 15 mg of natural lycopene and 0.5 mg to 3.5 mg of one or more additional carotenoid selected from among phytoene and/or phytofluene. Said oral dosage form may further comprise 1.5 mg to 8 mg of vitamin E. Preferably, said oral dosage form comprises 5 mg of natural lycopene, 0.5 mg phytoene, 0.45 mg phytofluene and 1.8 mg of vitamin E. Said dosage form may further contain a pharmaceutically acceptable adjuvant, excipient, carrier, filler, stabilizer or additive.

The present invention further relates to foodstuff or beverages which contains a carotenoid composition as described herein. The foodstuff or beverage contain 5 mg to 15 mg of natural lycopene and 0.5 mg to 3.5 mg of one or more carotenoid selected from among a group consisting of phytoene and phytofluene. Said food-stuff or beverage may further contain 1.5 mg to 8 mg of vitamin E. Preferably, said food-stuff or beverage comprises 4.1 mg of natural lycopene, 2.2 mg phytoene, 1.6 mg phytofluene and 3.8 mg of vitamin E.

The present invention presents the following advantages:
1. The compositions do not contain pro-vitamin A carotenoids, which at certain elevated dosages may be a health hazard. Thus, the present invention is safer and does not have the health risks as compositions described in the prior art.
2. The protection is provided via in-vivo activity. Thus, the protective composition cannot be washed away or depleted like topical protective compositions.
3. The compositions of the present invention have been shown to have improved bioavailability compared to other sources of natural lycopene and in comparison to synthetic lycopene, and thus offer improved protection against uv light-induced skin damage.
4. The composition may bring about tanning of the skin to a brown hue in subjects exposed to uv radiation without the damages associated with uv radiation. This has both health and aesthetic advantages.

EXAMPLES

Example 1: Preparation of Carotenoid Composition

The lycopene used throughout the Examples is natural lycopene by LycoRed®.

Formulation 1: Each Capsule Contains:

| | |
|---|---|
| Lycopene | 4.88 mg |
| Phytoene | 0.48 mg |
| Phytofluene | 0.44 mg |
| Vitamin E | 1.81 mg | in soft gel capsules which are prepared according to standard procedures known to the skilled artisan.

Formulation II: Each Soft Drink Bottle Contains

| | |
|---|---|
| Lycopene | 4.1 mg |
| Phytoene | 2.2 mg |
| Phytofluene | 1.6 mg |
| Vitamin E | 3.8 mg |

Formulation III

| | |
|---|---|
| Lycopene | 5.5 mg |
| Vitamin E | 2.0 mg |

Example 2: Comparative Example of Protection Against Erythema

Three treatment groups consumed the following lycopene supplements for 12 weeks:
a) Group 1—Lyc-O-Mato® soft gel capsules[1] (1 capsule twice a day)
b) Group 2—Lyc-O-Guard™ drink[2] (250 ml bottle twice a day)
c) Group 3—Synthetic lycopene hard shell capsules[3] (1 capsule twice a day)
1) The carotenoid fraction is a tomato extract containing natural lycopene, phytoene, phytofluene and tocopherols. 2) The carotenoid fraction is a tomato extract similar to Lyc-O-Mato® which is further enriched with phytoene, phytofluene and tocopherols. 3) The carotenoid fraction contains synthetic lycopene and tocopherols.

The minimal erythema dose (MED), which is the minimal dose of uv radiation which produces a minimal erythema (reddening of the skin) after 24 hours was determined by exposing different small areas of skin to increasing doses of uv radiation. The testing of the effectiveness of the carotenoid supplementation was tested by exposing the subjects to 1.25 of the individual MED at 0, 4 and 12 weeks from the beginning of lycopene supplementation. The effect of the radiation on the reddening and pigmentation of the skin was measured by a Minolta chronometer. The "a" and "b" value of the chronometer correlate to the reddening and pigmentation of the skin, respectively. The erythema (reddening) was determined 24 hours after radiation of uv radiation, by subtracting the value of "a" before radiation from the value of "a" 24 hours after radiation. The value obtained is denoted by "Δa". Larger values of Δa correlate with increased erythema of the skin. FIG. 1 clearly demonstrates the improved protective effect against uv induced erythema, Lyc-O-Mato and Lyc-O-Guard have over synthetic lycopene.

While embodiments of the invention have been described by way of illustration, it will be apparent that the invention may be carried out with many modifications, variations and adaptations, without departing from its spirit or exceeding the scope of the claims.

The invention claimed is:

1. A method for protecting the skin of a subject against damages caused by ultra-violet (uv) radiation from the sun, comprising oral administration of an effective amount of composition to said subject, wherein said oral administration of said composition consists of administering said composition, wherein said composition consisting essentially of (a) a carotenoid fraction that has 6% to 15%, by weight relative to the weight of the composition lycopene and 0.3% to 1.5%, by weight relative to the weight of the composition phytoene, phytofluene, or mixtures thereof; and (b) 1.5% to 2.5%, by weight relative to the weight of the composition vitamin E, wherein said composition is devoid of pro-vitamin A carotenoid, thereby protecting the skin of the subject against damages caused by UV radiation from the sun;

wherein said administering begins 7 to 30 days before exposure to uv radiation.

2. The method according to claim 1, wherein said 0.3% to 1.5% by weight of phytoene, phytofluene, or mixtures thereof consists of 0.5% by weight of said phytoene and 0.5% by weight of said phytofluene.

3. The method according to claim 1, wherein said composition raises the carotenoid serum level of the subject to a level within the range of 0.3 to 1.2 µM.

4. The method according to claim 3 wherein carotenoid serum levels of the subject reaches a level of about 1.2 µM.

5. The method according to claim 1, wherein said composition is formulated for oral administration via foodstuff or beverage.

* * * * *